United States Patent [19]

Mayhew et al.

[11] 4,336,385
[45] Jun. 22, 1982

[54] PHOSPHATE IMIDAZOLINIUM COMPOUNDS

[75] Inventors: Raymond L. Mayhew, Summit; Anthony J. O'Lenick, Jr., Fairlawn, both of N.J.

[73] Assignee: Mona Industries, Inc., Paterson, N.J.

[21] Appl. No.: 137,197

[22] Filed: Apr. 4, 1980

Related U.S. Application Data

[62] Division of Ser. No. 965,458, Nov. 30, 1978, Pat. No. 4,209,449.

[51] Int. Cl.$^3$ .............................................. C07F 9/65
[52] U.S. Cl. .................................................. 548/112
[58] Field of Search ................ 548/112, 119; 544/157, 544/243

[56] References Cited

U.S. PATENT DOCUMENTS 3,856,893  12/1974  Diery et al. .................... 548/112
4,215,064  7/1980  Lindemann et al. ............ 548/112
4,243,602  1/1981  O'Lenick, Jr. et al. .......... 260/945
4,261,911  4/1981  Lindemann et al. ............ 260/945
4,283,542  8/1981  O'Lenick, Jr. et al. .......... 548/112

*Primary Examiner*—John M. Ford
*Assistant Examiner*—N. Harkaway
*Attorney, Agent, or Firm*—Felfe & Lynch

[57] ABSTRACT

Novel phosphate quaternary compound of the formula

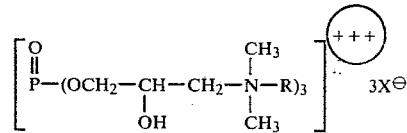

wherein
R is a tertiary amine radical of from 6 to 40 carbon atoms; and
X is an anion.

2 Claims, No Drawings

PHOSPHATE IMIDAZOLINIUM COMPOUNDS

This is a division of Ser. No. 965,458 filed Nov. 30, 1978, now U.S. Pat. No. 4,209,449.

BACKGROUND OF THE INVENTION

The present invention relates to novel compositions of matter consisting of specific quaternary compounds linked to a fully esterified phosphate group. These phosphate quaternary compounds, are formally cationics due to the nature of the phosphate triester.

Phosphate esters and quaternary compounds are known in the industry, but prior to this invention, compounds such as the phosphate quaternaric of the invention were not suggested. These products exhibit outstanding foaming, viscosity-building, wetting, cleansing, detergency, anti-static conditioning, emulsifying and bateriostatic properties. These highly stable compounds are well tolerated by human tissue (i.e., they exhibit exceptionally low oral toxicity and ocular irritation) hence they are eminently suited for use in cosmetic as well as industrial applications.

THE INVENTION

The novel phosphate quaternary compounds of this invention conform to the following general formula:

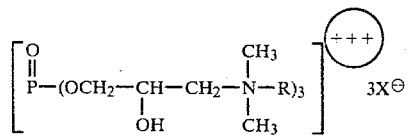

wherein R is a tertiary amine radical of at least 6 carbons. This carbon atom limitation serves to include only materials of significant hydrophobic properties. The R radical can be cyclic or non-cyclic, aliphatic, aromatic or heterocyclic; X is an anion, such as a halide, e.g., chloride.

In addition to the foregoing definitions wherein R is amidoamine,

R may be an N-heterocyclic radical which may contain one additional hetero atom (e.g., oxygen or another nitrogen) and contains 5 to 6 total ring carbon atoms; optionally said heterocyclic radical may be substituted with alkyl and/or hydroxyalkyl of up to 20 carbon atoms each. Typical of such N-heterocyclic radicals are imidazolyl, N-alkylmorpholino, alkylpyrimidino, alkyloxazolinyl, and the like. Such compounds may be represented by the formula:

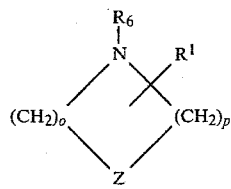

wherein
Z is N, S or O
o is an integer from 0 to 3
p is an integer from 1 to 3, provided that the sum of o+p is from 3 to 4
$R^1$ is alkyl, alkenyl, alkoxy or hydroalkyl of from 5 to 22 carbon atoms each, or aryl or alkaryl of up to 20 carbon atoms and is linked to a ring carbon atom, and
$R^6$ is alkyl of from 2 to 6 carbon atoms which may be substituted with a hydroxyl group at the terminal or a non-terminal carbon atom,
Y may be alkylene, optionally interrupted by up to 3 oxygen atoms, of up to 12 carbon atoms, which alkylene chain may optionally be substituted with lower alkyl, alkoxy, hydroxy or hydroxyalkyl, e.g., of not more than 10 carbon atoms each.

The quaternary compounds of the invention are prepared by reacting the corresponding amine and phosphate triester halide, as follows:

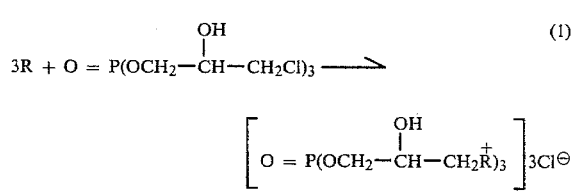

Preparation of Intermediate "R" Reactants

The amine reactant "R" applicable to synthesis (1) is, in general, prepared by reacting an acid with an aminoalkyl-substituted tertiary amine to result in the amidoamine function. Alternatively, an acid can be reacted with an aminoalkyl-substituted secondary amine, followed by further treatment of the reaction product with alkylene oxide. Finally, when R represents the N-heterocyclic structure, e.g., imidazolyl, this can be prepared in accordance with known techniques, e.g., as taught in U.S. Pat. No. 2,267,965.

Reaction (2) below yields the non-cyclic reactants "R" and Reaction (3) illustrates the preparation of a typical cyclic amine reactant R (imidazolyl):

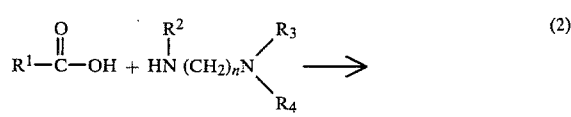

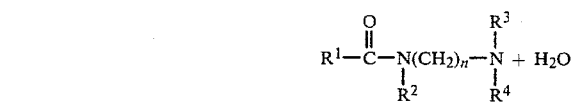

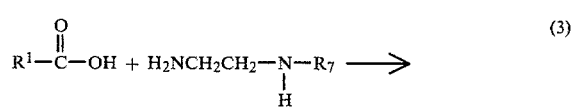

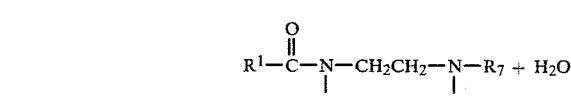

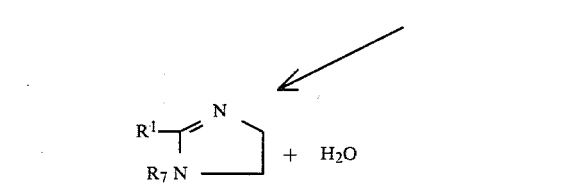

wherein
$R^1$ is defined as above and $R^7$ is alkyl of 2 to 6 carbon atoms which may be substituted with a hydroxyl group (at the terminal or a non-terminal carbon atom). This cyclic reactant can be prepared as disclosed in U.S. Pat. No. 2,267,965.

A vast variety of tertiary amines which are items of commerce are also used for preparation. Alkyl dimethyl amine, di and tri alkyl amines, ethoxylated amines are examples.

Preparation of Intermediate Tri Ester Reactants

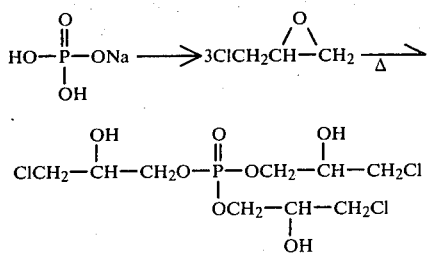

This reactant is prepared via the following method. To 60.00 parts of water charge 12.01 parts of mono sodium phosphate in a suitable reaction vessel under good agitation. Apply heat to 50°–55° C. Slowly charge 27.9 parts epichlorohydrin. Seal reactor and apply 5 psig $N_2$. Heat slowly to 80°–85° C. and hold 2 to 3 hours. Reaction is complete when acid value has been reduced to vanishingly small levels. Inorganic chloride levels will likewise be vanishingly small.

The above reactant was found to be reactive toward certain nucleophilic species, particularly to amines. If an amine of sufficiently hydrophobic character is chosen a surface active agent is obtained when reaction (1) is used to produce the novel phosphate quaternary compounds.

The compounds of this invention were tested by a "Cylinder Shake Test" for the evaluation of foaming characteristics.

In these test solutions containing 1.1% by weight of the candidate surfactant in water of 100 ppm hardness (calcium to magnesium ratio 3:2) were used and placed in 100 ml stoppered cylinders which had been cleaned so that water drains down its walls in an unbroken film. Each cylinder filled with test solution was shaken twenty (20) times in a standard manner and net foam in ml is noted one minute and again five minutes after shaking. The tests were run in triplicate. The results were as follows:

|  | Example Number | One Minute | Five Minutes |
|---|---|---|---|
| Current Products |  |  |  |
| Cocobetaine | — | 65 | 56 |
| Cocamidobetaine | — | 70 | 63 |
| "Monateric CSH-32"* | — | 66 | 54 |
| Novel Products |  |  |  |
| "Monaquat D"* | 3 | 90 | 83 |
| "Monaquat C"* | 9 | 98 | 90 |

The compatibility of the compounds with human tissue, i.e., eye tissue was tested. In these tests, a 0.1 ml sample of a neutral solution of the compound under investigation is dropped into one eye of an albino rabbit, the other eye serving as a control. Six rabbits are employed for each compound.

Observations are made after 1 day, 2 days, 3 days, 4 days and 7 days after initial instillation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjuctiva on a scale of 1 to 6 with a higher number indicating greater ocular irritation and the scores are added to give a total numerical value for each reading for 6 rabbits and average. The averaged score is an indication of the irritation potential of the composition under test. Based on the averaged score, descriptive irritation evaluation may be given, e.g., none, slight, moderate, severe, etc.

Typical results for a quaternary and a quaternary in accordance with the present invention when subjected to the above test procedure are as follows:

|  | Ocular Irritation Potential Days | | | | | Primary Dermal Irritation |
|---|---|---|---|---|---|---|
|  | 1 | 2 | 3 | 4 | 7 |  |
| Comparison Product |  |  |  |  |  |  |
| Stearyl di-methylbenzyl ammonium Chloride | 34 | 29 | 27 | 27 | 37 | 3.75 |
| Novel Product |  |  |  |  |  |  |
| "Monaquat S" (Example #4) | 4 | 2 | 0 | 0 | 0 | 1.1 |

As can be easily seen from the above data, Monaquat S is a very slight irritant while the stearyl di-Methylbenzyl ammonium chloride is a severe irritant.

These novel "MONAQUAT" products attribute viscosity building and conditioning properties as demonstrated by wet comb out tests.

The novel MONAQUATS were incorporated at 1% active into a standard Baby Shampoo formulation (Mona Technical Bulletin No. 960):

| TEARLESS BABY SHAMPOO | % by Weight |
|---|---|
| Water | 48.6 |
| Monateric CSH-32 | 40.0 |
| Monateric ISA-35 | 11.4 |
|  | 100.0 |

These formulations were evaluated for (1) viscosity using a Brookfield viscosmeter (spindle #4 at 20 RPMS) and (2) for conditioning properties. Conditioning properties were evaluated via a wet comb out test on hair swatches as per the following procedure.

Wet Comb-Out Test on Hair Swatches

Purpose: A laboratory screening method for determining the wet comb-out properties of shampoos under simulated use conditions.

Equipment: Hair swatches are prepared from a purchased supply of human hair from the same head. Each swatch contains 7 grams of hair, 11 inches in length. The hair is tied tightly with string an inch from one end, then bound firmly by wrapping with many laps of adhesive tape. Each swatch is identified by numbering with indelible ink on the tape.

Equipment (continued)
Rat-tail comb
Stop Watch
Paper Towelling 400 ml Tall Form Beaker Precleaning Solution: 3% Active Ammonium Lauryl Sulfate Test Solution: For a shampoo: 10 grams of shampoo in 90 grams tap water.

Procedure
(1) Thoroughly wash the swatch by dunking 20 times in the lauryl sulfate precleaning solution.
(2) Rinse under running tap water at about 40° C., using the spray attachment.
(3) Squeeze out excess water by drawing the swatch between pinched finger tips.
(4) Apply the test solution while the hair is still damp by dunking 20 times in 200 ml of test solution at room temperature.
(5) Rinse with 40° C. running tap water using spray attachment.
(6) Excess water is again removed with finger tips.
(7) Blotting with paper towelling.
(8) Hang swatch, using opened-out paper clip as hanger.
(9) While holding the swatch with the finger tips comb swatches as rapidly as possible, on alternate sides, measuring the seconds required with a stop watch.
(10) Keep combing until the comb passes freely in one long stroke from top to bottom without snagging.
(11) Observe the time required.

Comments
(1) Each test solution should be evaluated with a minimum of three swatches.
(2) Swatches should be precleaned before each use unless testing for build-up.
(3) Typical results range from 12-15 seconds for shampoos or rinses with excellent comb-out to 60-75 seconds with poor comb-out properties.

The results were as follows:

| Added Monaquat | Example No. | Viscosity at pH = 6.5 | Time in Seconds For Wet Comb-Out Test Dilution 5g/100 |
|---|---|---|---|
| Control (water added) | | 1,900 CPS | 31 |
| Monaquat D | 3 | 3,000 CPS | 26 |
| Monaquat C | 9 | 3,200 CPS | 16 |
| Monaquat S | 4 | 7,600 CPS | 5 |

The MONAQUAT Compounds, when evaluated by themselves, make good rinse conditioners. Wet comb out tests were conducted using the MONAQUAT at 0.2% active. The following results are typical.

| RINSE CONDITIONER (WET COMB OUT TEST) | | |
|---|---|---|
| Experimental Addition (0.2% Active) | Example No. | Time in seconds |
| Monaquat D | 3 | 7 |
| Monaquat C | 9 | 9 |
| Monaquat S | 4 | 14 |
| Control (tap water) | | 26 |

As can be seen from the above results, these novel quaternary compounds attribute significant viscosity and conditioning properties. This, in addition to then outstanding foaming properties and low ocular and dermal irritation, makes these products extremely applicable for cosmetics industry.

The following examples are presented to show how compounds of the MONAQUAT family can be prepared. They are presented merely for illustration and are not meant to limit the invention.

EXAMPLE #1

To 60.00 parts of soft water in a suitable reactor, charge 12.01 parts of the Reactant under good agitation. Heat to 45°–50° C. and slowly charge 27.99 parts of cocamidopropyl dimethyl amine under good agitation. Heat to 90°–95° C. and hold for 4-5 hours. Reaction is complete when inorganic chloride reaches theoretical and residual tertiary nitrogen levels are vanishingly small.

The product is an aqueous solution of the material shown below:

$$\overset{O}{\underset{\|}{P}}-(OCH_2-\overset{OH}{\underset{|}{CH}}-CH_2\overset{\oplus}{\underset{\underset{CH_3}{|}}{N}}-CH_2CH_2CH_2-\overset{H}{\underset{|}{N}}-\overset{}{\underset{\|}{C}}-R)_3$$

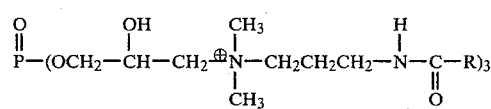

R = C7 to C17 alkyl

EXAMPLE #2

To 60.00 parts of soft water in a suitable reactor, charge 12.29 parts of the Reactant under good agitation. Heat to 45°–50° C. and slowly charge 27.71 parts of lauramidopropyl dimethyl amine under good agitation. Heat to 90°–95° C. and hold for 4-5 hours. Reaction is complete when inorganic chloride reaches theoretical and residual tertiary nitrogen levels are vanishingly small.

The product is an aqueous solution of the material shown below:

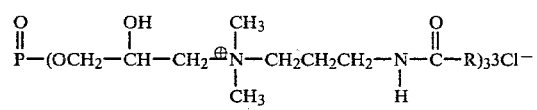

R = C11 alkyl.

EXAMPLE #3

To 60.00 parts of soft water in a suitable reactor, charge 11.50 parts of the Reactant under good agitation. Heat to 45°–50° C. and slowly charge 28.50 parts of myristamidopropyl dimethyl amine under good agitation. Heat to 90°–95° C. and hold for 4-5 hours. Reaction is complete when inorganic chloride reaches theoretical and residual tertiary nitrogen levels are vanishingly small.

The product is an aqueous solution of the material shown below:

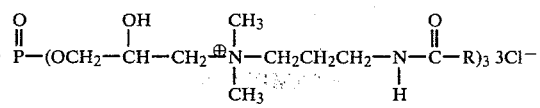

R = C13 alkyl.

EXAMPLE #4

To 60.00 parts of soft water in a suitable reactor, charge 10.19 parts of the Reactant under good agitation. Heat to 45°–50° C. and slowly charge 29.81 parts of stearamidopropyl dimethyl amine under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

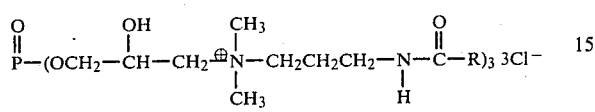

R = $C_{17}$ alkyl.

EXAMPLE #5

To 60.00 parts of soft water in a suitable reactor, charge 14.28 parts of the Reactant under good agitation. Heat to 45°–50° C. and slowly charge 25.72 parts of alkyl dimethyl amine (alkyl = $C_{12}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

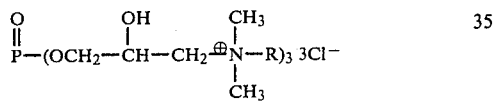

R = $C_{12}$ alkyl.

EXAMPLE #6

To 60.00 parts of soft water in a suitable reactor, charge 13.22 parts of the Reactant under good agitation. Heat to 45°–50° C. and slowly charge 26.78 parts of alkyl dimethyl amine (alkyl = $C_{14}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

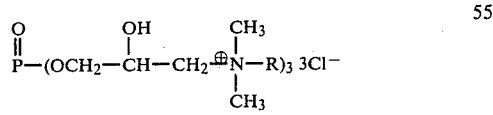

R = $C_{14}$ alkyl.

EXAMPLE #7

To 60.00 parts of soft water in a suitable reactor, charge 12.32 parts of the Reactant under good agitation. Heat to 45°–50° C. and slowly charge 27.68 parts of alkyl dimethyl amine (alkyl is $C_{16}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

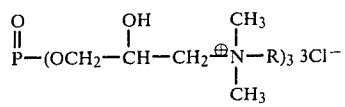

R = $C_{16}$ alkyl.

EXAMPLE #8

To 60.00 parts of soft water in a suitable reactor, charge 10.50 parts of the Reactant under good agitation. Heat to 45°–50° C. and slowly charge 29.5 parts of 1-hydroxyethyl 2-alkyl imidazoline (alkyl being $C_{17}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

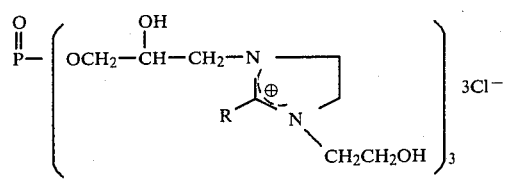

R = $C_{17}$ alkyl.

EXAMPLE #9

To 60.00 parts of soft water in a suitable reactor, charge 12.17 parts of the Reactant under good agitation. Heat to 45°–50° C. and slowly charge 27.88 parts of 1-hydroxyethyl 2-alkyl imidazoline (alkyl being $C_7$ to $C_{17}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

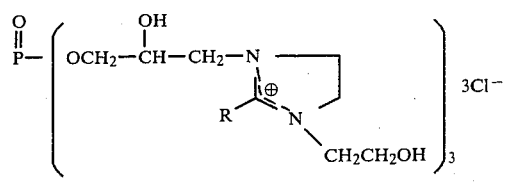

R = $C_7$–$C_{17}$ alkyl

EXAMPLE #10

To 60.00 parts of soft water in a suitable reactor, charge 10.70 parts of the Reactant under good agitation. Heat to 45°–50° C. and slowly charge 29.30 parts of 1-hydroxyethyl 2-alkyl imidazoline (alkyl being $C_{17}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

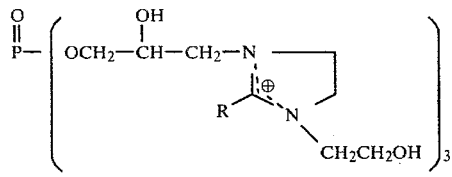

R = C₁₇ alkyl

EXAMPLE #11

To 60.00 parts of soft water in a suitable reactor, charge 9.72 parts of the Reactant under good agitation. Heat to 45°–50° C. and slowly charge 30.28 parts of 1-hydroxyethyl 2-alkyl imidazoline (alkyl being 70% $C_{11}$/30% $C_{13}$) under good agitation. Heat to 90°–95° C. and hold for 4–5 hours. Reaction is complete when inorganic chloride reaches theoretical and residual tertiary nitrogen levels are vanishingly small.

The product is an aqueous solution of the material shown below:

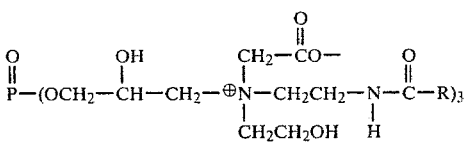

R = 70% $C_{11}$
30% $C_{13}$

What is claimed is:
1. Phosphate quaternary compound of the formula

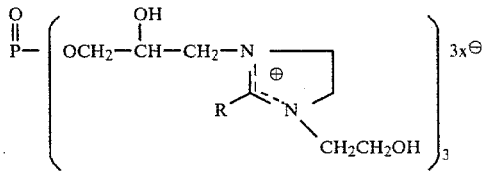

wherein
x represents chloride, and
R represents an alkyl group of seven to seventeen carbon atoms.
2. Compound of claim 1 wherein R is a $C_{17}$ alkyl group.

* * * * *